United States Patent
Fong et al.

(10) Patent No.: US 6,479,294 B1
(45) Date of Patent: Nov. 12, 2002

(54) METHOD FOR DETERMINING CONTAINER LEAKAGE

(75) Inventors: Wendy Fong, Alhambra, CA (US); Naoki Ota, Stevenson Ranch, CA (US); Hisashi Tsukamoto, Saugus, CA (US)

(73) Assignee: Quallion LLC, Sylmar, CA (US)

( * ) Notice: Subject to any disclaimer, the term of this patent is extended or adjusted under 35 U.S.C. 154(b) by 0 days.

(21) Appl. No.: 09/705,375

(22) Filed: Nov. 2, 2000

(51) Int. Cl.[7] .............................................. G01N 31/00
(52) U.S. Cl. ........................ 436/3; 436/161; 73/45.5; 73/49.3
(58) Field of Search .......................... 436/3, 2, 56, 148, 436/161; 422/68.1; 73/45.5, 49.3, 49.2, 40, 52; 429/90; 324/432, 434

(56) References Cited

U.S. PATENT DOCUMENTS

| | | | | |
|---|---|---|---|---|
| 2,479,743 A | * | 8/1949 | Hall | 73/45.5 |
| 2,961,869 A | * | 11/1960 | Bagno | 73/45.5 |
| 4,089,208 A | * | 5/1978 | Franks et al. | 73/45.5 |
| 5,447,688 A | * | 9/1995 | Moore | 422/56 |
| 5,759,857 A | * | 6/1998 | Goyal et al. | 436/3 |
| 5,922,943 A | * | 7/1999 | Chapman, IV | 73/40.7 |

* cited by examiner

Primary Examiner—Jill Warden
Assistant Examiner—Sam P. Siefke
(74) Attorney, Agent, or Firm—M. Elizabeth Bush; Freilich, Hornbaker & Rosen

(57) ABSTRACT

A method and apparatus suitable for use in high volume production for determining leakage from a nominally sealed product container, e.g., a battery case. The method and apparatus first functions to analytically test for leakage of a particular component of interest, e.g., a liquid electrolyte comprising a mixture of ethylene carbonate (EC) and methyl-ethyl carbonate (MEC) in a lithium-ion battery. A second gas leakage test can then be performed.

21 Claims, 4 Drawing Sheets

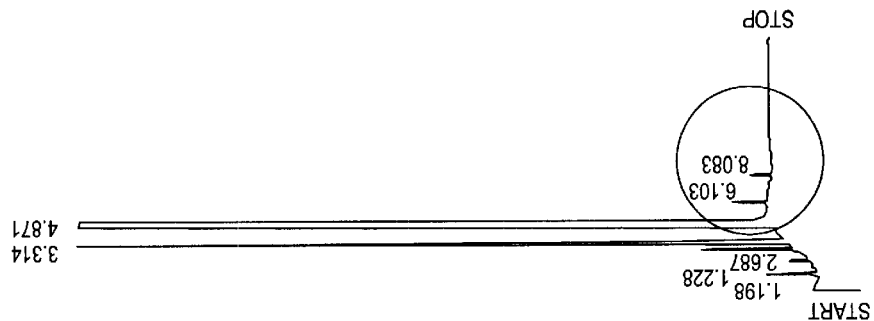
FIG. 5 CASE WITH LEAKS
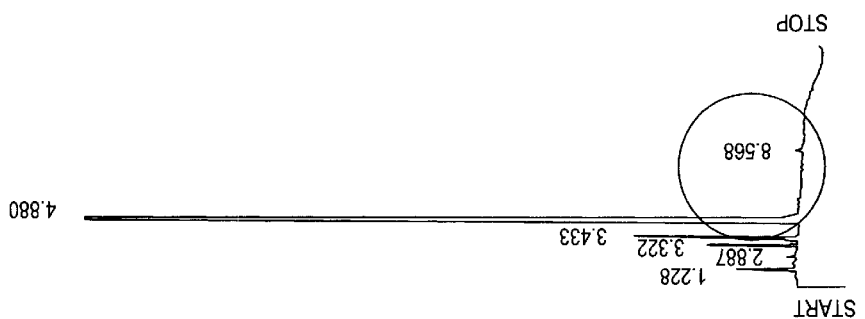
FIG. 4 RINSE BLANK
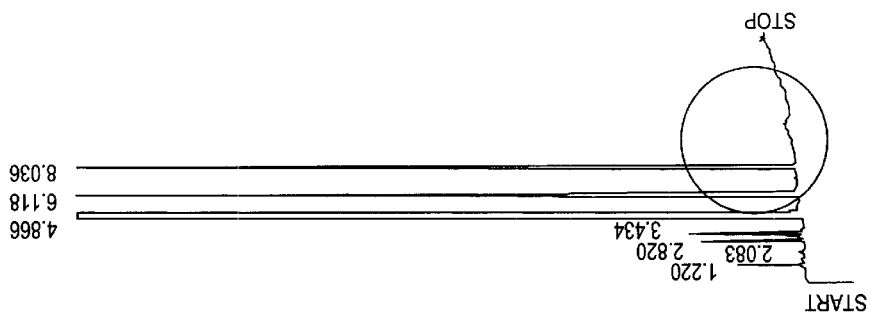
FIG. 3 REFERENCE STANDARD

METHOD FOR DETERMINING CONTAINER LEAKAGE

FIELD OF THE INVENTION

This invention relates generally to a method for determining leakage from a nominally sealed product container. The container, for example, can comprise the case of an electrochemical battery but more generally can comprise any product container containing a liquid component, e.g., electrolyte. A method in accordance with the invention is primarily intended for batch testing multiple product units in the manufacturing process of batteries and the like for detecting leakage sufficiently slow as to be unapparent to the naked eye.

BACKGROUND OF THE INVENTION

For battery and capacitor manufacturers, it is of utmost importance from a safety and reliability standpoint, that the product case be properly sealed. A variety of commercially available leak testing apparatus and methods exist that attempt to measure leak rates including electronic sensors, helium leak detectors, pH measurement devices, and visual inspection. Electronic sensors typically have detection limits in the parts per ten thousand range and are usually complex and not practical for high volume processing. High-end helium leak detectors have detection limits of $10^{-10}$ cc-atm/sec. However, if the leak opening is greater than the helium atom but smaller than the molecules of the leak component of interest, helium easily escapes the product container and the test results in a false negative. Another method measures chemical behavior that can be differentiated along the pH scale. This method is qualitative and limited to small families of chemicals that are pH sensitive. Finally, the traditional method of visual inspection, either by the naked eye or through optical microscope, is magnification and speed limited. For example, the conventional visual inspection method involves placing batteries in a controlled temperature environment for several days or weeks. Signs of leakage would typically show as marks of residual chemical corrosion and the like on the surface of the battery case emanating from the leakage point. In mass production, this method is labor-intensive and quite costly.

SUMMARY OF THE INVENTION

The present invention is directed to a method and apparatus suitable for use in high volume production for determining leakage from a nominally sealed product container, e.g., a battery case. More particularly, the invention is directed to a method and apparatus for analytically testing for leakage of a particular component of interest, e.g., a liquid electrolyte comprising a mixture of ethylene carbonate (EC) and methyl-ethyl carbonate (MEC) in a lithium-ion battery.

A method in accordance with the invention first requires that the product container be cleaned to remove measurable traces of the leakage component of interest. The cleaned container is then placed in a sealed vessel containing an extraction medium compatible with the leakage component. The extraction medium should be miscible with the leakage component and readily separable from the leakage component using commercially available separation apparatus, e.g., gas chromatograph. After one or more predetermined time intervals, a sample of the extraction medium is collected from the vessel. The collected sample is then analyzed in a high sensitivity chromatography system to determine the concentration of the leakage component of interest. Leakage rate can then be determined based on the measured concentration and the known time interval. If the leakage rate exceeds a certain threshold, the product is rejected.

In accordance with a preferred embodiment of the invention, a product container which passes the aforedescribed first leakage test stage is preferably subjected to a second stage which tests for gas leakage. This second stage presumes that the product container in fabrication was sealed in the presence of a gas such as helium, argon, nitrogen and the like. In order to test for leakage from the container, the container is placed into a test cavity which is evacuated to a very low negative pressure. Leakage from the container is then monitored over time to detect presence of the gas in which the container was originally sealed, e.g., helium or argon or nitrogen.

BRIEF DESCRIPTION OF THE DRAWINGS

FIG. 3 depicts a reference chromatograph chart;

FIG. 4 depicts a chart similar to FIG. 3 for a final product container rinse;

FIG. 5 depicts a chart similar to FIG. 3 for a leaky product container; and

DETAILED DESCRIPTION

Figure 1:
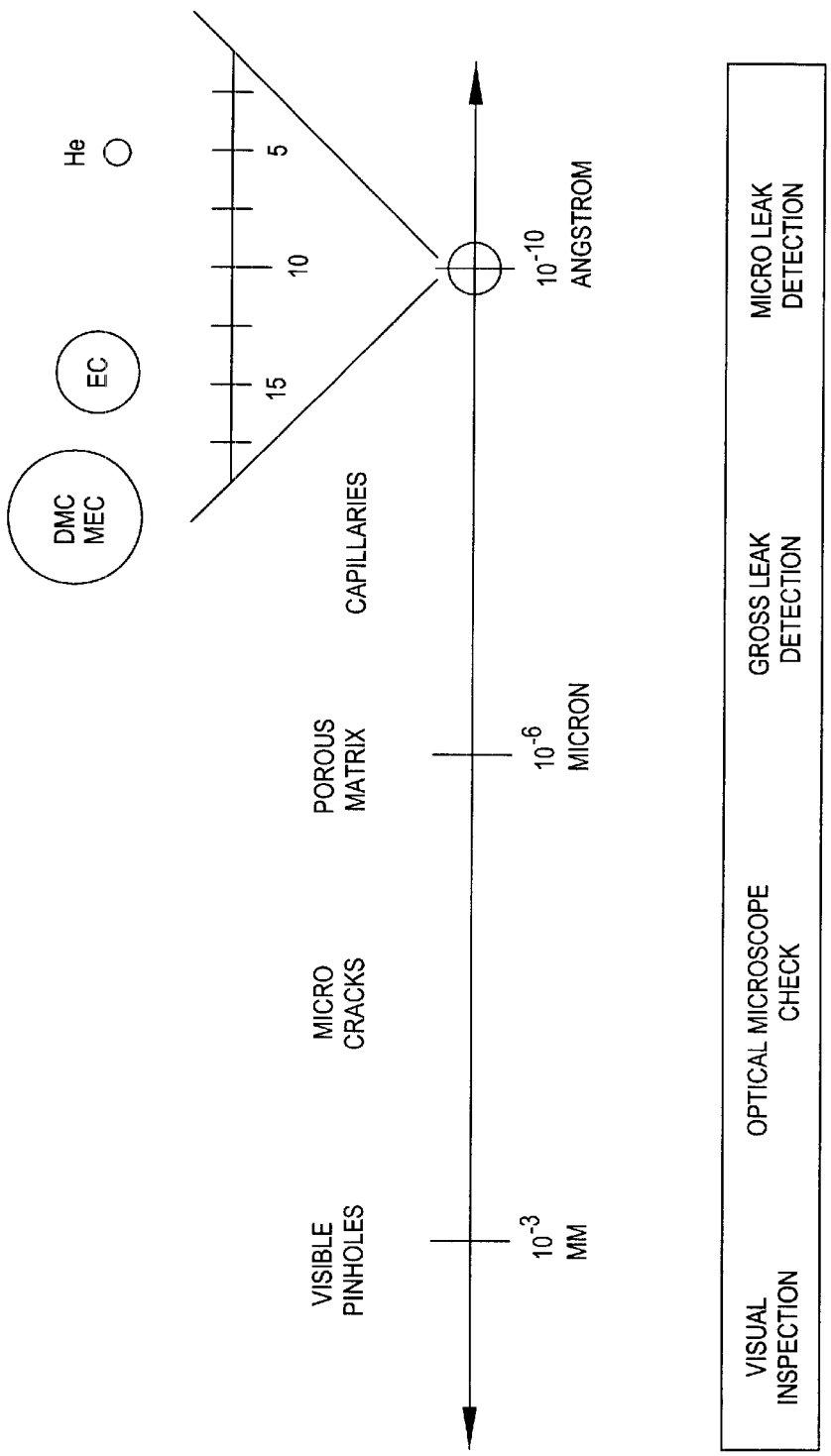
FIG. 1 diagrammatically represents possible causes of container leakage and shows dimensional ranges for each.

FIG. 1 diagrammatically represents various possible causes of container leakage and depicts approximate dimensional ranges for each type of leakage path. Thus, FIG. 1 depicts that leakage paths can be attributable to visible pinholes, micro-cracks, porous matrix material, and capillaries respectively dimensioned, as shown, from millimeter size ($10^{-3}$ meter) to micron size ($10^{-6}$ meter) to angstrom size ($10^{-10}$ meter). Visual naked eye and/or microscope inspection is often adequate to determine leakage in the millimeter range. Methods in accordance with the present invention are useful for detecting leakage in the micron range (i.e., gross leak detection) and in the angstrom range (i.e., micro leak detection).

Figure 2:
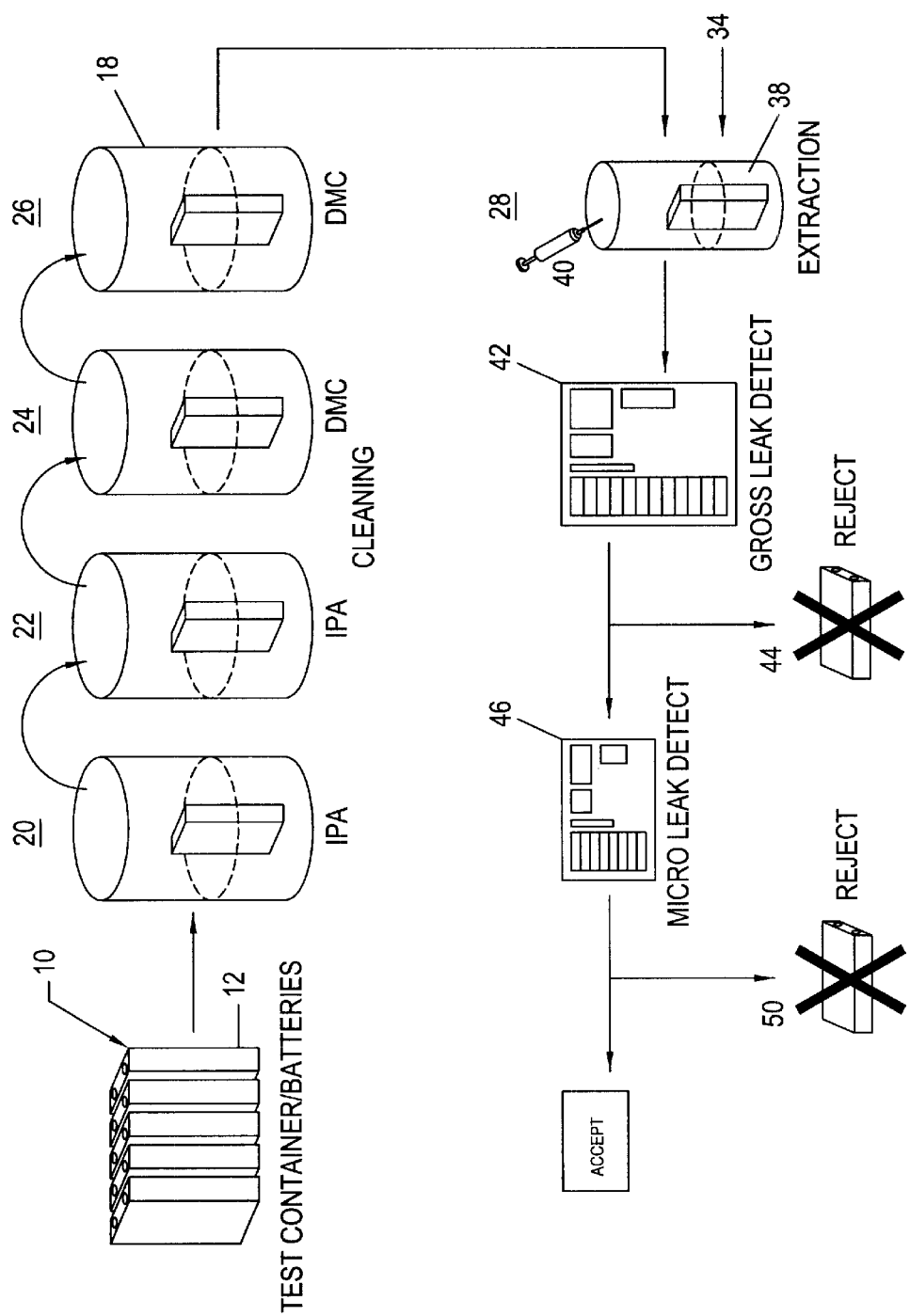
FIG. 2 depicts a process flow chart in accordance with a preferred embodiment of the invention for detecting leakage through a battery case.

FIG. 2 depicts a preferred method in accordance with the invention for detecting leakage from a nominally sealed container, e.g., a battery rinsed with isopropyl alcohol (IPA) (steps 20, 22) flowed by two rinses with dimethyl carbonate (DMC) (steps 24, 26) to remove contaminants accumulated during fabrication and handling. Dimethyl carbonate was selected as the rinsing solvent of choice for its solubility and compatibility with the leakage components of interest, which include electrolyte components, EC and MEC. A sample of the final rinse is preferably tested using a gas chromatograph with FID and a wax column. The peaks of interest (EC and MEC) are not present as shown in the chromatograph of FIG. 4 relative to the reference chromatograph of FIG. 3.

The batteries are then placed in sealable glass bottles 34 filled with an extraction medium 38 comprising 0.3 ml of DMC. Extraction is then allowed to occur over one or more timed intervals at 20EC. As shown in FIG. 5, a leaking battery would be apparent by the conspicuous appearance of the peaks of interest (EC and MEC) as compared to the lack of peaks in FIG. 4.

Figure 6:
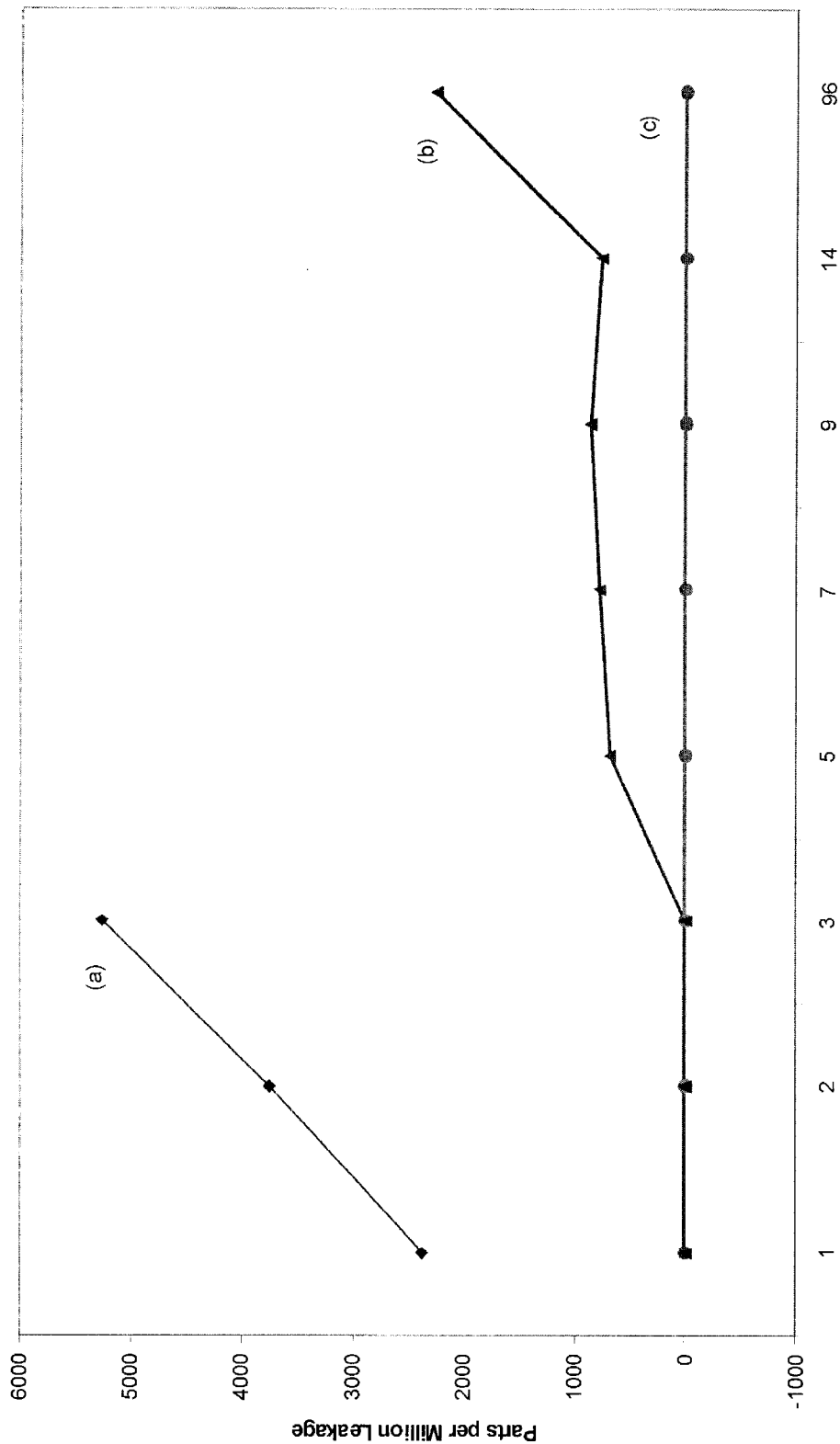
FIG. 6 depicts a graph plotting battery leakage as a function of time for three different samples.

FIG. 6 demonstrates that certain leaks occur immediately (plot (a)), whereas others may appear only after an extended period of extraction, which can be accelerated with elevated temperature and/or pressure. In this example, the leakage rate for battery (b) is extremely slow as the leakage appears only after the fifth hour of extraction. After 96 hours, battery sample (c) continues to show no leakage.

The invention has been described in detail with reference to a particular preferred process, but it should be understood that variations and modifications will occur to those skilled in the art well within the intended spirit and scope of the invention.

We claim:

1. A method for determining leakage from a nominally sealed case containing a first component, said method comprising:
   cleaning said case to remove traces of said first component;
   providing a sealed vessel containing an extraction medium compatible with said first component;
   placing said case in said sealed vessel;
   collecting a sample of said extraction medium from said vessel after a certain time interval; and
   analyzing said collected sample to determine the concentration of said first component in said extraction medium, wherein said analyzing step includes separating said first component from said extraction medium using chromatography.

2. The method of claim 1 including the further step of determining the leakage rate of said first component into said extraction medium.

3. The method of claim 2 including the further step of rejecting a case if its leakage rate exceeds a certain threshold.

4. The method of claim 1 including a further step of placing said case into a scaled evacuated test cavity; and
   monitoring pressure variations in said cavity to indicate gas leakage from said case.

5. The method of claim 4 including the further step or rejecting a case if its leakage rate exceeds a certain threshold.

6. A production method for testing a battery comprised or a case containing a liquid electrolyte to detect for leakage of said electrolyte, said method comprising:
   cleaning said case to remove exterior traces of said electrolyte;
   providing a sealed vessel containing an extraction medium compatible with said electrolyte;
   placing said case in said sealed vessel in contact with said extraction medium for a certain time interval;
   collecting a sample from said sealed vessel after said interval; and
   analyzing said collected sample to determine the concentration of said electrolyte therein.

7. The method of claim 6 including a further step of determining leakage rate or said electrolyte into said extraction medium.

8. The method of claim 6 including a further step of placing said case into a sealed evacuated test cavity; and
   monitoring pressure variations in said cavity to indicate gas leakage from said case.

9. The method of claim 6 wherein said electrolyte comprises a mixture of ethylene carbonate (EC) and methylethyl carbonate (MEC); and wherein
   a solution of dimethyl carbonate (DMC) is provided as said extraction medium.

10. The method of claim 6 wherein said cleaning stop comprises rinsing said case in successive rinse solutions.

11. The method of 10 wherein said electrolyte comprises a mixture or ethylene carbonate (EC) and methyl-ethyl carbonate (MEC); and wherein one of said rinse solutions comprises dimethyl carbonate (DMC).

12. A leak detection method comprising the steps of:
    placing an electrolyte solution comprising ethylene carbonate and methylethyl carbonate into a container;
    placing the container in contact with a dimethyl carbonate solution for a certain time interval to allow some of the electrolyte solution to leak out of the container and into the dimethyl carbonate solution if a leak exists in the container;
    collecting a sample comprising some of a solution of the dimethyl carbonate solution and leaked electrolyte solution, if any; and
    analyzing the collected sample to determine the presence of ethylene carbonate and methyl-ethyl carbonate therein.

13. A leak detection method comprising the steps of:
    placing an electrolyte solution comprising ethylene carbonate and methylethyl carbonate into a container;
    rinsing the container in dimethyl carbonate solution;
    placing the container in contact with an extraction medium for a certain time interval to allow some of the electrolyte solution to leak out of the container and into the extraction medium if a leak exists in the container;
    collecting a sample comprising some of a solution of the extraction medium and leaked electrolyte solution, if any; and
    analyzing the collected sample to determine the presence of ethylene carbonate and methyl-ethyl carbonate therein.

14. The method of claim 1 and further comprising the steps of:
    placing said case into a sealed, evacuated test cavity; and
    monitoring for the presence of a gas in which the case was sealed.

15. The method of claim 14 wherein said gas comprises He, Ar, or N.

16. The method of claim 6 and further comprising the steps of:
    placing said case into a sealed, evacuated test cavity; and
    monitoring for the presence of a gas in which the case was sealed.

17. The method of claim 16 wherein said gas comprises He, Ar, or N.

18. The method of claim 6 and further comprising the step of:
    performing a battery formation process whereby gas is formed thereby creating a positive internal pressure within said case.

19. The method of claim 6 wherein said analyzing step includes separating extraction medium and electrolyte components using chromatography.

20. The method of claim 6 wherein said analyzing step includes detecting an electrolyte component using a detection apparatus chosen from the group consisting of mass spectroscopy, ultraviolet detector, and flame-ionization detector.

21. The method of claim 1 wherein said analyzing step includes detecting said first component using a detection apparatus chosen from the group consisting of mass spectroscopy, ultraviolet detector, and flame-ionization detector.

* * * * *

UNITED STATES PATENT AND TRADEMARK OFFICE
CERTIFICATE OF CORRECTION

PATENT NO. : 6,479,294 B1
DATED : November 12, 2002
INVENTOR(S) : Wendy Fong et al.

It is certified that error appears in the above-identified patent and that said Letters Patent is hereby corrected as shown below:

Column 2,
Line 43, after the word "battery" insert the following: -- or capacitor case, containing a liquid, e.g., an electrolyte. Although methods in accordance with the invention have wide application, for purposes of illustration and clarity herein, a preferred embodiment will be described which is particularly suited for batch testing lithium-ion batteries as part of an overall battery manufacturing process. Such lithium-ion batteries can be filled, for example, with a liquid electrolyte comprising a mixture of ethylene carbonate (EC) and methyl-ethyl carbonate (MEC) while in a controlled environment rich in an appropriate gas such as helium, argon or nitrogen. The nominal size of EC and MEC molecules is 20 Å. The size of a helium atom is about 5 Å. A preferred method in accordance with the invention includes a first test stage which tests for leakage of the electrolyte liquid molecules and a second test stage which tests for leakage of the environmental gas.

Figure 2 illustrates a sequence of steps to be performed with respect to one or more products, e.g., batteries 10, each comprised of a container or case 12 defining an outer envelope or barrier. A leakage path through the case could adversely effect the life and reliability of the product, and accordingly it is important during the manufacturing process to identify and reject products exhibiting excessive leakage paths.

With reference to Figure 2, the outer surface of each case 12 is first cleaned to remove traces of the leakage component of interest, e.g., the electrolyte. Cleaning is accomplished by rinsing each case 12 in a suitable solvent 16 contained in a vessel 18 at an appropriate temperature for a sufficient interval. Preferably, multiple cleaning steps 20, 22, 24, 26 are provided for sequentially intimately contacting each case 12 with one or multiple solvents. The temperature (e.g., 10°C to 60°C) utilized and the interval defined for each step preferably enables the multiple steps to exhibit sequentially enhanced solubility as a case 12 moves sequentially through the steps. Although, Figure 2 depicts only a single case in each vessel 18 for purposes of illustration, it should be understood that in practice it is contemplated that the cases move through the process steps in batches of multiple product units.

After completion of cleaning steps 20, 22, 24, 26, extraction step 28 is performed in which case 12 is placed inside a vessel 34 sealable by cover 36. The vessel 34 contains an extraction medium 38, which can comprise an appropriate liquid or gas, intended to intimately contact the case 12 at a predetermined temperature and pressure favorable to the extraction process. The extraction medium 38 is selected to be miscible with the leakage component of interest, e.g., the aforementioned liquid electrolyte mixture of EC, MEC. The extraction medium selected should be separable from the leakage component of interest using commercially available separation apparatus. Temperature should be adjusted based on the time available for executing the test and temperature toleration of the case and/or its components. Pressure for the extraction should be set such that the pressure inside the extraction vessel 34 is equal to or less than the pressure inside case 12.

UNITED STATES PATENT AND TRADEMARK OFFICE
CERTIFICATE OF CORRECTION

PATENT NO.     : 6,479,294 B1
DATED          : November 12, 2002
INVENTOR(S)    : Wendy Fong et al.

It is certified that error appears in the above-identified patent and that said Letters Patent is hereby corrected as shown below:

During the extraction step 28, liquid-liquid and/or liquid-vapor diffusion occurs across the barrier between the liquid in the case 12 and the extraction medium 38 via any leakage path through the barrier, i.e. case 12. Samples of the solution (extraction medium and leakage component), are collected after one or more predetermined extraction intervals. The collected samples are then analyzed using a commercially available high-sensitivity chromatography system 42. The system 42 comprises an effective separation medium such as a column, a carrier medium such as liquid or gas, and a detection apparatus such as flame-ionization detector (FID). Examples of high sensitivity chromatography systems include a gas chromatograph with FID, a high performance liquid chromatograph with ultraviolet detector, and a gas chromatograph with mass spectrometer or any combination thereof. The concentration of the leakage component of interest is first determined and then leak rate is calculated by dividing the concentration by the known extraction time interval. The leakage component can be determined by comparing the sample chromatograph with a reference chromatograph (see Figures 3-5), or in the case when an identification apparatus such as a mass spectrometer is employed, the unknown peak may be deduced from its characteristic ionization pattern. If the calculated leakage rate exceeds a certain threshold, the product under test is rejected (step 44). On the other hand if the leakage rate is below that certain threshold, the product is then preferably subjected to a second stage micro-leak detection step 46.

In step 46, the product is introduced into a test cavity which is preferably evacuated to a very low negative pressure. Leakage is detected by monitoring for the presence of the gas in which the product case was sealed, e.g., helium, argon, or nitrogen. If the case leaks, then the product is rejected at step 50.

The aforedescribed method can be used in a variety of applications for testing a product container for leakage. In one particularly useful example, the aforedescribed method is used as part of the process of high volume manufacturing of lithium-ion batteries. Such batteries are used in a wide variety of applications where small size and light weight are significant. For example only, lithium-ion batteries are frequently employed in implantable devices for medical applications. Such situations typically demand high reliability and long life.

As a specific example, consider a production line manufacturing lithium-ion batteries having a volume on the order of 175 $cm^3$ each and containing a liquid electrolyte mixture comprising $LiPF_6$, ethyl carbonate (EC) and methyl-ethyl carbonate (MEC). The case of each battery typically includes mechanical seals and welded seals formed in the manufacturing process in a controlled environment of at least 25% helium gas.

UNITED STATES PATENT AND TRADEMARK OFFICE
CERTIFICATE OF CORRECTION

PATENT NO. : 6,479,294 B1
DATED : November 12, 2002
INVENTOR(S) : Wendy Fong et al.

It is certified that error appears in the above-identified patent and that said Letters Patent is hereby corrected as shown below:

After sealing, the batteries are preferably subjected to a typical routine procedure for formation. It is recommended that the batteries be tested for leakage after formation as this procedure often results in gas formation within the battery, creating a slightly positive internal pressure. In accordance with the method of the invention, as shown in Figure 2, the batteries are first cleaned, twice--;

Column 3,
Line 32, change "or" to -- of --;
Line 35, change "or" to -- of --;
Line 50, change "or" to -- of --;
Line 61, change "stop" to -- step --;

Column 4,
Line 5, change "methylethyl" to -- methyl-ethyl --;
Line 19, change "methylethyl" to -- methyl-ethyl --.

Signed and Sealed this

Fifteenth Day of April, 2003

JAMES E. ROGAN
*Director of the United States Patent and Trademark Office*